US006662048B2

United States Patent
Balczewski et al.

(10) Patent No.: US 6,662,048 B2
(45) Date of Patent: Dec. 9, 2003

(54) IMPLANTABLE MEDICAL DEVICE WITH TEMPERATURE MEASURING AND STORING CAPABILITY

(75) Inventors: Ron A. Balczewski, Roseville, MN (US); Jeffrey A. Von Arx, Minneapolis, MN (US); William J. Linder, Golden Valley, MN (US); Mark D. Amundson, Cambridge, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 99 days.

(21) Appl. No.: 09/823,260

(22) Filed: Mar. 30, 2001

(65) Prior Publication Data

US 2002/0143371 A1 Oct. 3, 2002

(51) Int. Cl.$^7$ .............................................. A61N 1/365
(52) U.S. Cl. ............................. 607/21; 600/549; 374/1
(58) Field of Search ................................. 607/17, 18, 21; 600/549; 374/1, 100

(56) References Cited

U.S. PATENT DOCUMENTS

| 4,519,401 A | 5/1985 | Ko et al. .................. 118/748 |
| 4,634,294 A | 1/1987 | Christol et al. ............. 374/170 |
| 4,803,987 A * | 2/1989 | Calfee et al. .................. 607/24 |
| 5,089,019 A | 2/1992 | Grandjean ..................... 623/3 |
| 5,109,853 A | 5/1992 | Taicher et al. ........... 128/653.2 |
| 5,486,200 A | 1/1996 | Lindemans ..................... 607/5 |
| 5,516,285 A | 5/1996 | Yacker et al. ................. 433/72 |
| 5,535,752 A * | 7/1996 | Halperin et al. ............ 600/483 |
| 5,598,847 A | 2/1997 | Renger ....................... 128/691 |
| 5,833,603 A | 11/1998 | Kovacs et al. .............. 600/317 |
| 5,904,708 A | 5/1999 | Goedeke ...................... 607/18 |
| 5,919,210 A | 7/1999 | Lurie et al. .................... 607/3 |
| 6,309,350 B1 * | 10/2001 | VanTassel et al. .......... 600/300 |

FOREIGN PATENT DOCUMENTS

| EP | 0168640 | 1/1986 | ............ G01K/1/02 |
| EP | 1050265 | 11/2000 | ............ A61B/5/00 |

* cited by examiner

*Primary Examiner*—Angela D. Sykes
*Assistant Examiner*—Roderick Bradford
(74) *Attorney, Agent, or Firm*—Schwegman, Lundberg, Woessner & Kluth, P.A.

(57) ABSTRACT

An implantable medical device such as a cardiac pacemaker or implantable cardioverter/defibrillator with the capability of storing body temperature measurements taken periodically and/or when triggered by particular events.

17 Claims, 2 Drawing Sheets

IMPLANTABLE MEDICAL DEVICE WITH TEMPERATURE MEASURING AND STORING CAPABILITY

FIELD OF THE INVENTION

This invention pertains to implantable medical devices such as cardiac rhythm management devices. In particular, the invention relates to a method and system incorporated into such a device for gathering clinically useful physiological data.

BACKGROUND

Implantable cardiac rhythm management devices are commonplace today for the treatment of chronic or recurring cardiac arrhythmias. For example, cardiac pacemakers are implantable devices that replace or supplement a heart's compromised ability to pace itself (i.e., bradycardia) due to chronotropic incompetence or a conduction system defect by delivering electrical pacing pulses to the heart. Implantable cardioverter/defibrillators (ICD's) are devices that deliver electrical energy to the heart in order to reverse excessively rapid heart rates (tachycardia) including life threatening cardiac arrhythmias such as ventricular fibrillation. Since some patients have conditions that necessitate pacing and also render them vulnerable to life-threatening arrhythmias, implantable cardiac devices have been developed that combine both functions in a single device.

Cardiac rhythm management devices are typically implanted subcutaneously or submuscularly in a patient's chest and have leads threaded intravenously into the heart to connect the device to electrodes used for sensing and pacing. Leads may also be positioned on the epicardium by various means. A programmable electronic controller causes shocks to be delivered when fibrillation is detected or pacing pulses to be output in response to lapsed time intervals and sensed electrical activity. Pacemakers sense intrinsic cardiac electrical activity by means of internal electrodes disposed near the chamber to be sensed.

Modern cardiac rhythm management devices also typically have the capability to communicate data via a data link with an external programming device. Such data is transmitted to the pacemaker in order to program its mode of operation as well as define other operating parameters. Data transmitted from the pacemaker can be used to verify the operating parameters as well as relay information regarding the condition of both the pacemaker and the patient. Pacemaker patients are monitored at regular intervals as part of routine patient care and to check the condition of the device. Among the data which may typically be telemetered from the pacemaker are its programming parameters and an electrogram representing the electrical activity of the heart as sensed by the pacemaker.

Pacemakers have also been developed which monitor a patient's exertion level while the device is functioning in order to adjust the pacing rate. Such devices, referred to as rate-adaptive pacemakers, may use various measurable physiological parameters for this purpose that are related to exertion level including minute ventilation, body activity, electrogram intervals, and body temperature. Because of their continuous access to the patient and their communications capabilities, cardiac rhythm management devices and other similar implantable devices may also offer an ideal platform for gathering and storing clinically useful information which can later be transmitted to an external device.

SUMMARY OF THE INVENTION

The present invention is a method and system for monitoring temperature in an implantable medical device such as a cardiac pacemaker or implantable cardioverter/defibrillator. Data from these monitoring operations can then be stored in the memory of the device for later retrieval using an external programmer. In one embodiment, temperature measurements are collected at specified regular intervals to ascertain trends in the patient's temperature that may be useful in diagnosing certain medical conditions. The collection intervals may be made shorter or longer in order to detect fast or slow trends, respectively. Temperature data may also be collected to reflect average temperature variations over specified periods (e.g., daily) and at specific times of the day. Averages of temperature measurements taken over a period of time can also be used to compensate for component drift in the temperature sensor by calibrating the temperature sensor to match an average temperature which is assumed to be consistently maintained by the body.

In another embodiment, temperature measurements are associated with contemporaneous physiological measurements such as heart rate, respiratory rate, and body activity as well as any device activity to aid the clinician in interpreting the data. Detection of certain events such as arrhythmias or initiation of particular device activities may be used to trigger measurement of temperature and possibly other physiological variables.

Body temperature measurements may be taken using a temperature sensor incorporated into an intravenous lead or otherwise external to the device. Alternatively, temperature sensing circuitry internal to the device housing may be employed to provide the temperature measurement. Because device activity can affect its internal temperature, the system may require that temperature measurements using an internal sensor only be taken during periods in which the device is not actively delivering therapy. In a particular embodiment of an internal sensor, a proportional-to-absolute-temperature (PTAT) current typically used by the device electronics to generate a reference voltage is employed as a temperature sensor. Incorporating a temperature sensor within the device housing allows a clinician to determine if the temperature is within an acceptable range before allowing the device to become operational in a patient and also allows monitoring of temperature before implantation to determine if temperature extremes have occurred during storage which may adversely affect device operation. As the internal temperature of an electronic device may change during certain activities, such as delivery of shock pulses in the case of an implantable cardioverter/defibrillator, either no temperature data is collected during such activities or such data is flagged accordingly.

Another embodiment of the invention involves efficient storage and transmission of temperature data. Because of the limited range of temperature measurements taken within the human body, the range and resolution of stored temperature data can be adjusted so that less storage space is needed and data can be transmitted more efficiently. A non-linear range can also be used so that different resolutions are used with different temperatures.

DETAIL DESCRIPTION

Figure 1:
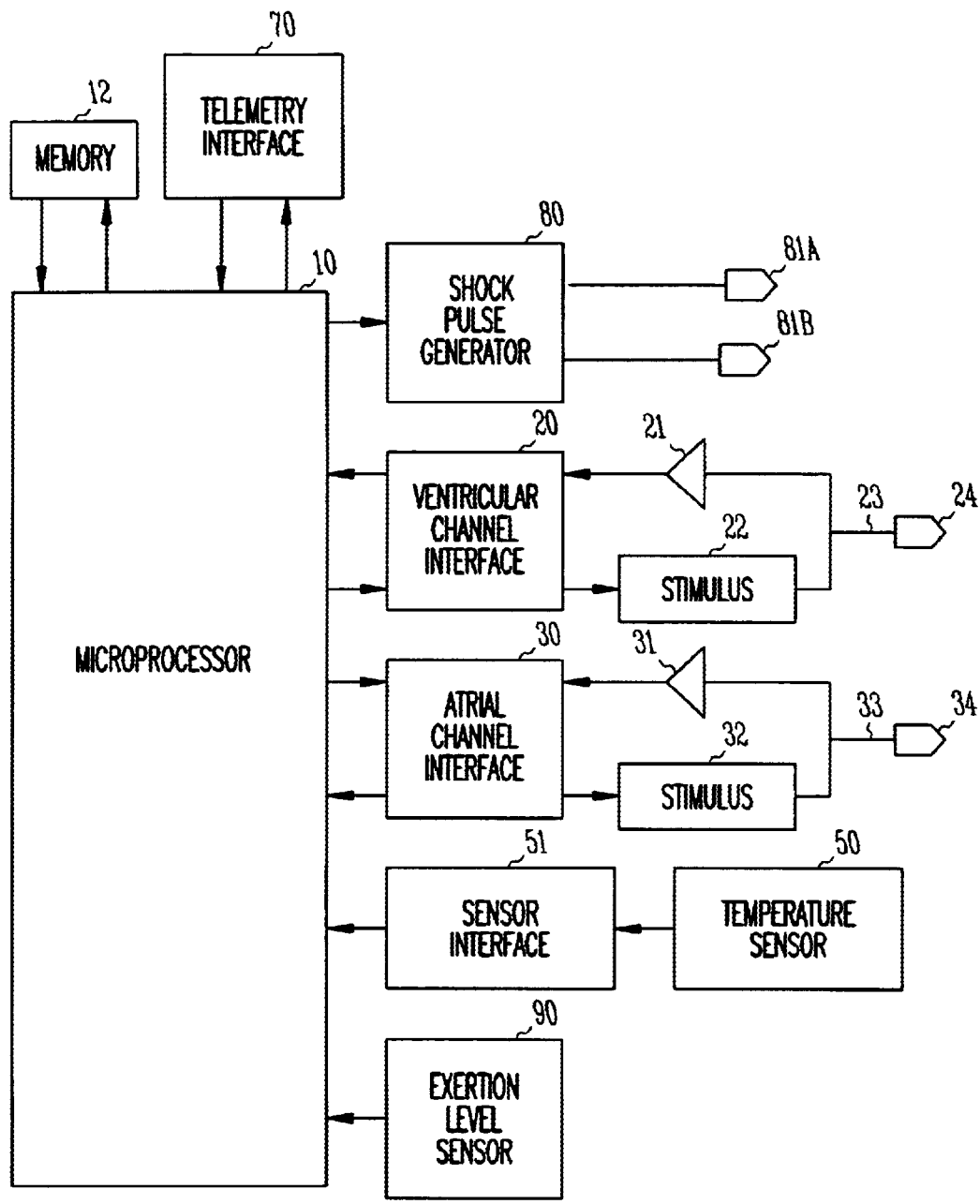
FIG. 1 is a system diagram of an implantable medical device incorporating the invention.

FIG. 1 shows a system diagram of an implantable medical device, in this case is a microprocessor-based pacemaker with defibrillation and/or antitachycardia pacing capability that incorporates the present invention. A microprocessor controller 10 communicates with a system memory 12 via a bidirectional system bus. Memory 12 may typically comprise a ROM for program storage and a RAM for data storage. The overall operation of the device is controlled by a system program running from the memory 12. The microprocessor also has a port for communicating with the telemetry interface 40 which in turn receives programming data from and transmits telemetry data to an external programmer 70 by a radio or other data link. The pacemaker has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The channel interfaces include sampling circuitry and an analog-to-digital converter for digitizing sensing signal outputs from the sensing amplifiers and registers which can be written to by the microprocessor in order to control pacing. An exertion level sensor 90 is also provided for rate-adaptive pacing. The exertion level sensor may measure, for example, respiratory rate, minute ventilation, or body activity with an accelerometer. A shock pulse generator 80 is also interfaced to the microprocessor for delivering defibrillation pulses to the heart via a separate pair of electrodes 81a and 81b.

A temperature sensor 50 communicates with the microprocessor via a sensor interface 51. The sensor 50 may be a resistive temperature detector driven by a current source that converts temperature changes in the patient's body into electrical signals. The sensor 50 may be incorporated into an external lead (e.g., an intravenous lead) or may be internal to the housing of the device. An example of such an internal sensor is described more fully below. The sensor interface 51 includes sampling circuitry for sampling the sensor output and an analog-to-digital converter for digitizing the samples that are then processed and stored by the microprocessor.

In accordance with the invention, the controller 10 is configured to store temperature measurements collected at specified regular intervals and/or collected when triggered by sensed events or initiation of particular device activity. For example, temperature measurements may be collected and stored at specified times on a daily basis with an associated time stamp. Other physiological measurements may also be simultaneously collected and associated with a temperature measurement, including measurements of heart rate, respiratory rate, minute ventilation, or body activity. A temperature measurement may also be triggered by other sensor activity such as when a measured exertion level measurement reaches a specified limit value or upon detection of a specified cardiac rhythm.

One use of periodic temperature measurements is to calculate a trend from the measurements indicating temperature changes over a specified period of time. The device can also be programmed to enable trending for a combination of heart rate, accelerometer measurements, respiratory rate, temperature, or other such inputs. Besides varying which inputs to trend, and the trending rate (e.g. fast/slow) can also be selectively varied, and each of the trended inputs could be sampled at an independent rate. For example, the heart rate could be sampled once every 16 seconds while the temperature is only sampled once every 15 minutes. The fast trending rate for the temperature could be once every 15 minutes and the slow trending rate could be once every hour. This trending data could then be read from the device on a daily or weekly interval depending on the trending rate. Another option is to gather trending information around some critical point in time. For example trending data could be gathered only around cardiac events or around patient activated times. Even if trending is not programmed, the basal temperature can still be recorded on a daily basis. This can be done by measuring the temperature at set time (e.g. 3 am) or after the patient activity is at a minimum (e.g. 2 hours at lower rate limit). This basal temperature data could be kept for the last 30 days or other specified time period.

Temperature sensors can drift over time due to component drift or such things as flicker noise. For example, when a PG is first calibrated it may read 98.8 deg as 98.7 degrees, and over time the error will vary. Over the life of the product the temperature error could be as much as a few degrees. As long as the error is known it can be subtracted from the indicated measurement in order to find the actual temperature. One method to do this automatically is to take advantage of the consistent average temperature of the human body. For example, if over a week the average temperature measured is 97.0 degrees, it could be assumed that the error term is −1.8 degrees. All the temperature measurements for the period can then be scaled up by 1.8 degrees. The temperature sensor can also be calibrated by programming the device with an actual temperature when measured by other means.

Temperature data collected as described above may be transmitted via the telemetry data link to an external programmer. After the temperature data has been transmitted, it can be further processed and graphically displayed. The further processing could include any of the following: adjusting temperature data to account for drift error in the measurement (i.e. autocalibration), comparing the temperature data to other previous data to determine trends, combining temperature data with device activity or other sensors, and plotting temperature verses a daily cycle or monthly cycle.

Figure 2:
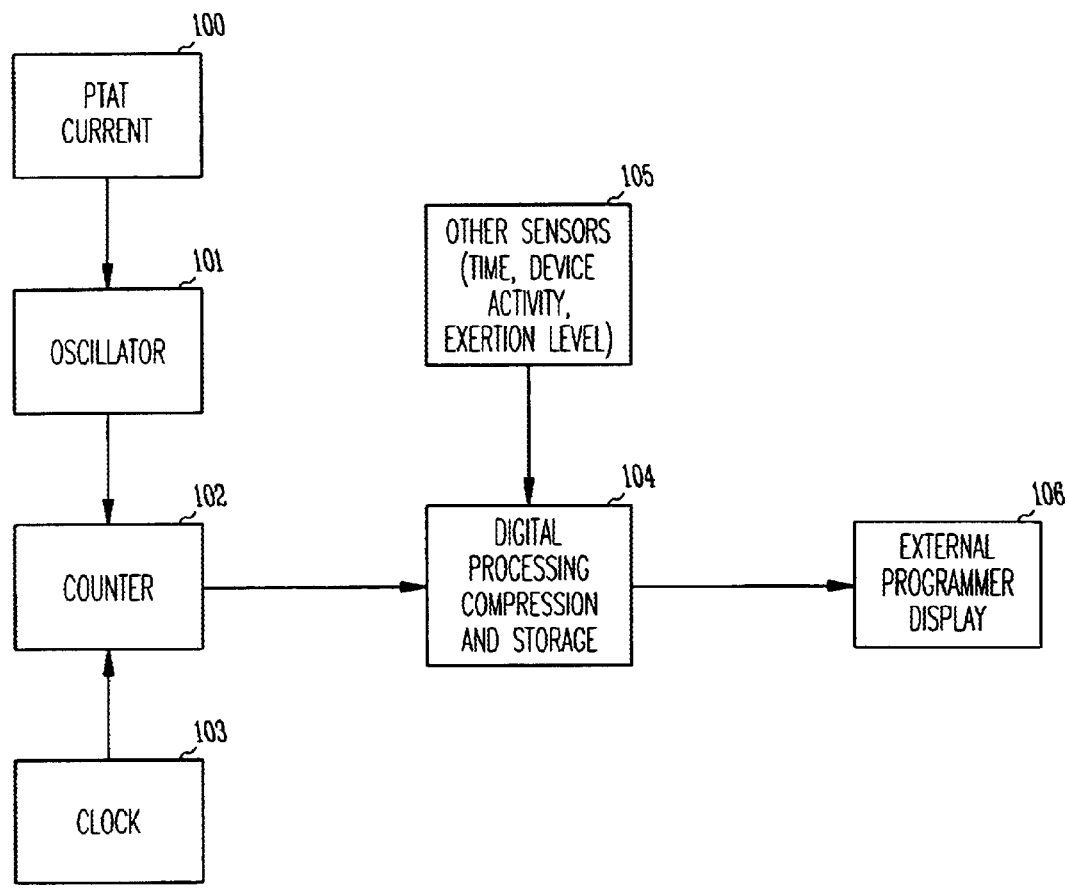
FIG. 2 is a block diagram of a particular implementation of an internal temperature sensor.

The temperature sensor 50 may either be incorporated into an intravenous lead or located within a housing for the sensor. The sensor may be of any convenient type such as a thermistor, resistive temperature detector, or thermocouple. A particular embodiment of a temperature sensing circuit internal to the device housing utilizes the proportional-to-absolute-temperature (PTAT) current typically generated by the device electronics. A PTAT current is normally used to generate a reference voltage with a bandgap reference voltage circuit, but also provides a convenient way of measuring the device temperature. Except when heat is being generated by the device, the device temperature is equilibrated with the body temperature so that the PTAT current varies with body temperature. FIG. 2 is a block diagram of a possible implementation of such a temperature sensor. A PTAT current source 100 feeds into an oscillator 101 that generates a clock signal with a frequency proportional to the IPTAT current. A counter 102 compares the oscillator clock frequency to a stable timebase such as could be generated by a crystal oscillator 103. The data out of the counter 102 is then a number that is proportional to temperature that is processed by circuitry 104 and which can be transmitted to an external programmer display 106. As described above, the temperature data may also be processed with signals from other sensors 105.

Incorporating the temperature sensor within the device housing means that the sensor is subject to heating caused by, for example, high currents when the device is delivering shock therapy or reforming the electrolytic capacitors used to deliver shock therapy. Temperature measurements may therefore be prohibited from being collected during such activity or within a specified time window afterward.

Alternatively, such temperature measurements may be flagged accordingly.

Having a temperature sensor incorporated into the device housing also allows monitoring of temperatures before implantation such as when the device is being stored for long periods of time. During storage of the device, for example, the temperature may be measured once per hour with an alarm flag set if the temperature ever leaves safe storage temperature limits. The flag can be announced whenever the device is interrogated. Minimum and maximum storage temperatures can also be logged. The device can also be configured to issue an alarm if the present device temperature is not inside the safe operational temperature limits. This can happen because the storage temperature limits are broader than the operational temperature limits. If for example, the device has been brought in from a very cold environment (such as outside winter temperatures) and has not had sufficient time to warm up, the device could be outside of the operational temperature limits but still within safe storage limits.

Another aspect of the invention involves the manner in which temperature data is represented which impacts both the required storage space and transmission bandwidth. One method of compressing the storage space and transmission bandwidth of temperature data is to assume a fixed offset or to use a nonlinear compression scheme. For example, if an 8 bit linear scale is used to store temperature data, then the scale could be from 0 to 127.5 degrees with 0.5 degree resolution which is too coarse a resolution. With 0.1 degree resolution, the temperature range would only be 0.0 to 25.5 degrees, which is too small. If a 90 degree offset were to be used, the temperature range would become 90.0 to 115.5 degrees with a 0.1 degree resolution. This means that the 8 bit number represents the difference between 90 degrees and the actual temperature reading (e.g. a temperature of 98 degrees would be represented as 180, so 90+180/10=98). This would yield good temperature resolution over a limited range. The range and resolution could be adjusted for recording different types of information (e.g. −40 degree offset, 1 degree resolution as a coarse temperature range). An example of a nonlinear range would be to use a different resolution depending on the temperature. For example temperatures between −40 to 90 and 116 to 178 could have resolutions of 2 degree, and temperatures between 90 and 115.4 could have resolutions of 0.2 degrees.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A medical device adapted for implantation into a patient, comprising:
   a temperature sensor for measuring a temperature within the patient's body;
   sampling circuitry and an analog-to-digital converter for sampling and digitizing temperature measurement;
   a controller for collecting and storing temperature measurements and for computing an average temperature measurement;
   wherein the controller is configured to calibrate the temperature sensor by adjusting sensor measurements by an amount equal to the difference between the average temperature measurement and a nominal temperature assumed to be maintained by the patient's body.

2. The device of claim 1 wherein the controller is further configured to store temperature measurements as specified times on a daily basis with an associated time stamp.

3. The device of claim 1 wherein the controller is further configured to store temperature measurements at specified intervals and calculate a trend from the measurements indicating temperature changes over a specified period of time.

4. The device of claim 1 further comprising a sensing channel for sensing cardiac electrical activity and wherein the controller is configured to measure heart rate and associate a temperature measurement with a simultaneously measured heart rate.

5. The device of claim 1 further comprising an exertion level sensor for measuring an exertion level and wherein the controller is configured to associate a temperature measurement with a simultaneously measured exertion level.

6. The device of claim 5 wherein the exertion level sensor is selected from a group consisting of a minute ventilation sensor, respiratory rate sensor, and a body activity sensor.

7. The device of claim 5 wherein the controller is configured to trigger a temperature measurement when a measured exertion level measurement reaches a specified limit value.

8. The device of claim 4 wherein the controller is configured to detect particular cardiac rhythms and to trigger a temperature measurement upon detection of a specified cardiac rhythm.

9. The device of claim 1 wherein the controller is configured to store the temperature data with a variable resolution depending upon the temperature.

10. The device of claim 1 further comprising an external lead and wherein the temperature sensor is incorporated into the external lead.

11. The device of claim 1 further comprising a housing for the device and wherein the temperature sensor is located within the housing.

12. A method for operating an implantable medical device, comprising:
    measuring a temperature within a patient's body with a temperature sensor;
    collecting and storing temperature measurements;
    computing an average temperature measurement from the stored measurements; and,
    calibrating the temperature sensor by adjusting sensor measurements by an amount equal to the difference between an average temperature measurement and a nominal temperature assumed to be maintained by the patient's body.

13. The method of claim 12 further comprising storing temperature measurements as specified times on a daily basis with an associated time stamp.

14. The method of claim 12 further comprising storing temperature measurements at specified intervals and calculating a trend from the measurements indicating temperature changes over a specified period of time.

15. The method of claim 12 further comprising sensing cardiac electrical activity, measuring heart rate, and associating a temperature measurement with a simultaneously measured heart rate.

16. The method of claim 12 further comprising transmitting temperature measurements to an external programmer.

17. The method of claim 12 further comprising measuring an exertion level sensor and associating a temperature measurement with a simultaneously measured exertion level.

* * * * *